United States Patent [19]

Kawashima et al.

[11] Patent Number: 5,322,780

[45] Date of Patent: Jun. 21, 1994

[54] PROCESS FOR PRODUCTION OF OMEGA 9 TYPE POLYUNSATURATED FATTY ACID

[75] Inventors: Hiroshi Kawashima, Ibaraki; Hideaki Yamada; Sakayu Shimizu, both of Kyoto, all of Japan

[73] Assignee: Suntory Limited, Osaka, Japan

[21] Appl. No.: 953,030

[22] Filed: Sep. 29, 1992

[30] Foreign Application Priority Data

Sep. 30, 1991 [JP] Japan .................................. 3-251966

[51] Int. Cl.$^5$ .......................... C12P 7/64; C12P 1/02; C12N 1/14
[52] U.S. Cl. .................................. 435/134; 435/171; 435/254.1; 435/911
[58] Field of Search ..................... 435/134, 171, 254.1, 435/135; 514/558, 458

[56] References Cited

U.S. PATENT DOCUMENTS

| | | | |
|---|---|---|---|
| 2,346,011 | 8/1940 | Damm | 435/134 |
| 4,783,408 | 11/1988 | Suzuki et al. | 435/254 |
| 4,857,329 | 8/1989 | Sako et al. | 514/558 |
| 4,870,011 | 9/1989 | Suzuki et al. | 435/134 |
| 5,026,644 | 6/1991 | Manoh et al. | 435/134 |
| 5,053,222 | 10/1991 | Takasu et al. | 514/458 |
| 5,093,249 | 3/1992 | Nakajima et al. | 435/134 |
| 5,128,250 | 7/1992 | Akimoto et al. | 435/134 |
| 5,128,250 | 7/1992 | Akimoto et al. | 435/134 |
| 5,164,308 | 11/1992 | Kyle | 435/135 |

FOREIGN PATENT DOCUMENTS

| | | | |
|---|---|---|---|
| 0223960 | 9/1986 | European Pat. Off. | 7/64 |
| 0276541 | 9/1987 | European Pat. Off. | 7/64 |
| 0332423 | 3/1989 | European Pat. Off. | 7/64 |
| 91/07498 | 5/1991 | PCT Int'l Appl. | 7/64 |

OTHER PUBLICATIONS

Ratledge, C., "Biochemical Society Transactions," vol. 17(6), Dec. 1989, pp. 1139–1141.
Kendrick, A.. et al., "Lipids," vol. 27(1), 1992, pp. 15–20.
Jareonkitmongkol, S., et al., "Applied and Environmental Microbiology," vol. 58(7), 1992, pp. 2196–2200.
Jareonkitmongkol, S., et al., "J. of General Microbiology," vol. 138, 1992, pp. 997–1002.
Shimizu, S., et al., "Biosynthesis of C-20 Polyunsaturated Fatty Acids by *Mortierella* Fungi," pp. 158–165.
Shimizu, et al., "Sesamin Is a Potent and Specific Inhibitor of Δ5 Desaturase in Polyunsaturated Fatty Acid Biosynthesis," Lipids, vol. 26(7), 1991, pp. 512–516.
Shimizu, et al., "Production of a novel Ω1-eicosapentaenoic acid by *Mortierella alpina* 1S-4 grown on 1-hexadecene," Arch. Microbiol., vol. 156, 1991, pp. 163–166.
Ratledge, "The Potential of Microorganisms for Oil Production—A Review of Recent Publications," in Proceeding for *World Conference on Emerging Technologies in the Fats and Oils Industry*, ed. by Baldwin, 1986, American Oil Chemists' Society, pp. 325–330.

*Primary Examiner*—Douglas W. Robinson
*Assistant Examiner*—Kristin Larson
*Attorney, Agent, or Firm*—Burns, Doane, Swecker & Mathis

[57] ABSTRACT

A process for production of omega 9 type polyunsaturated fatty acid or a lipid containing the fatty acid, comprising the steps of culturing a microorganism having an ability to produce omega 9 type polyunsaturated fatty acid or a lipid containing said fatty said, and recovering the omega 9 type polyunsaturated fatty acid or the lipid containing said fatty acid.

12 Claims, No Drawings

PROCESS FOR PRODUCTION OF OMEGA 9 TYPE POLYUNSATURATED FATTY ACID

BACKGROUND OF THE INVENTION

Field of the Invention

The present invention provides a process for production of omega 9 type highly polyunsaturated fatty acid or a lipid containing said fatty acid. The fatty acid preferably contains at least two double bonds and has 18 to 22 carbon atoms.

Related Art

It is known that omega 9 type polyunsaturated fatty acids such as mead acid, eicosadienoic acid and the like are present as constituent fatty acids of tissues of an animal having essential fatty acid deficiency. However, since an amount of these fatty acids is very low, it is very difficult to isolate and purify them. Moreover, the presence of these fatty acids in the microbial field has never been known. Such a type of polyunsaturated fatty acids can be a precursor of 3-series leakotrienes, and therefore biological activities thereof are potentially useful. Therefore, there is a need for the development of a process for developing a large amount of omega 9 type highly polyunsaturated fatty acids.

Accordingly, the present invention provides a simple and efficient process for production of omega 9 type polyunsaturated fatty acids.

SUMMARY OF THE INVENTION

Accordingly, the present invention provides a process for production of omega 9 type polyunsaturated fatty acid comprising the steps of:
culturing a microorganism having an ability to produce omega 9 type polyunsaturated fatty acid to produce omega 9 type polyunsaturated fatty acid or a lipid containing omega 9 type polyunsaturated fatty acid, and
recovering the omega 9 type polyunsaturated fatty acid.

The present invention also provides a process for production of a lipid containing omega 9 type polyunsaturated fatty acid comprising the steps of:
culturing a microorganism having an ability to produce omega 9 type polyunsaturated fatty acid to produce a lipid containing omega 9 type polyunsaturated fatty acid, and
recovering the lipid containing omega 9 type polyunsaturated fatty acid.

Further, the present inventors found that when a microorganism having an ability to produce omega 9 type polyunsaturated fatty acid is cultured in a medium supplemented with a precursor of omega 9 type polyunsaturated fatty acid, for example, hydrocarbon, fatty acid, ester of fatty acid, salt of fatty acid, or an oil or fat containing said fatty acid, the productivity of omega 9 type polyunsaturated fatty acid is enhanced significantly.

Accordingly, the present invention provides a process for production of omega 9 type polyunsaturated fatty acid comprising the steps of:
culturing a microorganism having an ability to produce omega 9 type polyunsaturated fatty acid in a medium supplemented with a precursor for omega 9 type polyunsaturated fatty acid selected from the group consisting of hydrocarbon, fatty acid, ester of fatty acid, salt of fatty acid and oil or fat containing such fatty acid or adding the precursor for omega 9 type polyunsaturated fatty acid to a medium in which said microorganism has been cultured and further culturing the microorganism to produce omega 9 type polyunsaturated fatty acid or a lipid containing omega 9 type polyunsaturated fatty acid, and
recovering the omega 9 type polyunsaturated fatty acid.

The present invention further provides a process for production of a lipid containing omega 9 type polyunsaturated fatty acid comprising the steps of:
culturing a microorganism having an ability to produce omega 9 type polyunsaturated fatty acid in a medium supplemented with a precursor for omega 9 type polyunsaturated fatty acid selected from the group consisting of hydrocarbon, fatty acid, ester of fatty acid, salt of fatty acid and oil or fat containing such fatty acid, or adding the precursor for omega 9 type polyunsaturated fatty acid to a medium in which said microorganism has been cultured and further culturing the microorganism to produce a lipid containing omega 9 type polyunsaturated fatty acid, and
recovering the lipid containing omega 9 type polyunsaturated fatty acid.

According to a preferred embodiment of the abovementioned processes, the microorganism having an ability to produce omega 9 type polyunsaturated fatty acid has $\Delta 5$ desaturation activity and $\Delta 6$ desaturation activity, and has reduced or lost $\Delta 12$ desaturation activity. In another embodiment of the present processes, the microorganism having an ability to produce omega 9 type polyunsaturated fatty acid has an ability to produce arachidonic acid (ARA) and has reduced or lost $\Delta 12$ desaturation activity.

DETAILED DESCRIPTION

In the present invention any microorganism having an ability to produce omega 9 type polyunsaturated fatty acid can be used. More particularly, microorganisms having $\Delta 5$ desaturation activity and $\Delta 6$ desaturation activity, and having reduced or lost $\Delta 12$ desaturation activity can be preferably used. Such microorganisms can be obtained, for example, by mutating a microorganism having an ability to produce ARA to generate a mutant having reduced or lost $\Delta 12$ desaturation activity. Microorganisms having an ability to produce ARA include those belonging to the genus Mortierella, Conidiobolus, Pythium, Phytophthora, Penicillium, Cladosporium, Mucor, Fusarium, Aspergillus, Rhodotorula, or Entomophthora. As microorganisms belonging to the genus Mortierella, there are mentioned microorganisms belonging to the subgenus Mortierella, such as *Mortierella elongata, Mortierella exigua, Mortierella hygrophila, Mortierella alpirna,* and the like. Microorganisms used in the present invention, having an ability to produce ARA and having reduced or lost $\Delta 12$ desaturase activity can be obtained by mutating the microorganisms having an ability to produce ARA.

For mutagenesis, irradiation of a microorganism with a mutagen, such as radiation (X-ray, $\gamma$-ray, neutron or ultraviolet light), high temperature treatment, and chemical mutagens may be used. In a mutagenizing procedure, microbial cells are suspended in an appropriate buffer, and a mutagen is added therein. The treated suspension is incubated for an appropriate time, diluted and plated on a solid medium such as agar medium to form colonies of mutated microorganisms.

As chemical mutagens, alkylating agents such as nitrogen mustard, methyl methanesulfonate (MMS), N-methyl-N'-nitro-N-nirosoguanidine (NTG); base analogs such as 5-bromouracil; antibiotics such as mitomycin C; base synthesis inhibitor such as 6-mercaptopurine; pigments such as proflavine; certain carcinogens such as 4-nitroquinoline-N-oxide; and others such as manganese chloride, potassium permanganese, nitrous acid, hydrazine, hydroxylamine, formaldehyde, and nitrofurane compounds may be mentioned. Microorganisms to be treated with a mutagen can be vegetative cells such as mycelium or spores.

A mutant belonging to the genus Mortierella, for example *Mortierella alpina* SAM 1861 (FERM BP-3590), can be used. *Mortierella alpina* SAM 1861 was deposited at the Fermentation Research Institute Agency of Industrial and Technology at 1-3, Higashi 1-Chome, Tsukuba-shi Ibaraki-ken 305, Japan on Sep. 30, 1991 as FERM BP-3590.

Omega 9 type polyunsaturated fatty acids include, for example, 6,9-octadecadieoic acid, 8,11-eicosadienoic acid, and 5,8,11-eicosatrienoic acid (mead acid).

For culturing a mutant used in the present invention, spores, mycelium or a previously cultured preculture is added to a liquid medium or solid medium. A liquid medium contains, as a carbon source, glucose, fructose, xylose, saccharose, maltose, soluble starch, molasses, glycerol, mannitol, or the like, alone or in combination. As a nitrogen source, an organic nitrogen source such as peptone, yeast extract, malt extract, meat extract, casamino acids, corn steep liquor or urea, and an inorganic nitrogen source such as sodium nitrate, ammonium nitrate, ammonium sulfate or the like can be used alone or in combination. In addition, if necessary, inorganic salts such as phosphates, magnesium sulfate, ferric or ferrous sulfate, cupric sulfate or the like, and minor nutrient components such as vitamins may be used.

Concentration of components in a culture medium should be such that it does not inhibit the growth of the microorganism. Generally and practically, a concentration of carbon source is 0.1 to 30% by weight, preferably 1 to 10% by weight, and a concentration of a nitrogen source is 0.01 to 5% by weight, and preferably 0.1 to 2% by weight. Temperature for culturing is 5° to 40° C., and preferably 20° to 30° C.; and a pH value of a medium is 4 to 10, and preferably 6 to 9. Culturing may be aeration/agitation culturing, shaking culture, or stationary culture. Culturing is usually continued for 2 to 10 days.

In the case wherein a microorganism is cultured in a solid medium, the medium comprises wheat bran, rice hulls, rice bran or the like supplemented with water in an amount of 50 to 100% by weight relating to the weight of solid materials. Culturing is carried out at 5° to 40° C., preferably 20° to 30° C. for 3 to 14 days. In this case, the medium can contain nitrogen sources, inorganic salts, and minor nutrient compounds, such as those described above.

According to the present invention, to accelerate an accumulation of omega 9 type polyunsaturated fatty acid, a substrate of omega 9 type polyunsaturated fatty acid can be added to a medium. As the substrates, hydrocarbons having 12 to 20 carbon atoms such as tetradecane, hexadecane and octadecane, fatty acids having 12 to 20 carbon atoms such as tetradecanoic acid, hexadecanoic acid and octadecanoic acid, or salts thereof, for example, sodium salt or potassium salt; fatty acid esters wherein the fatty acid moiety has 12 to 20 carbon atoms, for example, a lower alkyl ester such as methyl ester, ethyl ester or propyl ester of such a fatty acid, and a lipid containing such fatty acids as its components, for example, olive oil, soybean oil, palm oil, coconut oil may be mentioned. They are used alone or in combination. Total amount of the precursor is 0.001 to 10% by weight per culture medium, and preferably 0.5 to 10% by weight per culture medium.

The additive can be added prior to inoculation of a producer microorganism or immediately after the inoculation. Alternatively, the additive can be added, after the culturing has started, to a culture medium in which the microorganism is growing or has been grown, followed by further culturing. Moreover, the additive can be added both prior to culturing and during culturing after the culturing has started. When the additive is added during culturing, the additive can be added once or more than one time, or continuously. The precursor can be the sole carbon source.

During the culturing, a large amount of lipid containing omega 9 type polyunsaturated fatty acid is intracellularly accumulated. When a liquid medium is used, omega 9 type polyunsaturated fatty acid is then recovered by a procedure, for example, described in the following.

After the culturing, the cultured cells are recovered by a conventional solid liquid separation means, such as centrifugation or filtering. The cells are thoroughly washed with water, and preferably dried. The drying can be carried out by lyophilization or air drying. The dried cells are extracted with an organic solvent, preferably in a nitrogen gas flow. As an organic solvent, ether such as ethyl ether, hexane, a lower alcohol such as methanol or ethanol, chloroform, dichloromethane, petroleum ether, or the like can be used. Moreover, an alternating extraction with methanol and petroleum ether, or an extraction with one phase solvent of chloroform-methanol-water can be successfully used. The solvent is distilled off from the extract under a reduced pressure to obtain a lipid containing omega 9 type polyunsaturated fatty acid in a high concentration.

Alternatively, wet cells can be extracted with a solvent miscible with water, such as methanol or ethanol, or a mixed solvent miscible with water, comprising said solvent and water and/or other solvent. Other procedures are the same as described above for dried cells.

The lipid thus obtained contains omega 9 type polyunsaturated fatty acid as a component of the lipid, such as fat. Although omega 9 type polyunsaturated fatty acid can be directly isolated, preferably it is isolated as an ester with a lower alcohol, for example, as methyl 8,11-eicosadienate, methyl 6,9-octadecadienoate, methyl ester of mead acid and the like. The esterification accelerates the separation of the target fatty acid from other lipid components, and from other fatty acids produced during the culturing, such as palmitic acid, oleic acid and linoleic acid (these fatty acids are also esterified simultaneously with the esterification of omega 9 type polyunsaturated fatty acid). For example, to obtain methyl ester of omega 9 type polyunsaturated fatty acid, the above-mentioned extract is treated with anhydrous methanol/HCl 5 to 10%, or $BF_3$/methanol 10 to 50% at room temperature for 1 to 24 hours.

Methyl ester of omega 9 type polyunsaturated fatty acid is recovered preferably by extracting the above-mentioned treated solution with an organic solvent such as hexane, ether such as ethyl ether, or ester such as ethyl acetate. Next, the resulting extract is dried on, for example, anhydrous sodium sulfate, and the solvent is distilled off preferably under reduced pressure to obtain a mixture comprising fatty acid esters. This mixture contains, in addition to methyl ester of omega 9 type polyunsaturated fatty acid, other fatty acid methyl esters, such as methyl palmitate, methyl stearate, methyl oleate and the like. To isolate methyl ester of omega 9 type highly polyunsaturated fatty acid from the mixture of these fatty acid methyl esters, column chromatography, low temperature crystallization, the urea-inclusion method, the liquid/liquid countercurrent chromatography method, and the like can be used alone or in combination.

To obtain omega 9 type polyunsaturated fatty acid from the methyl ester of omega 9 type polyunsaturated fatty acid, the latter is hydrolyzed with an alkali and freed omega 9 type polyunsaturated fatty acid is then extracted with an organic solvent for example ether such as ethyl ether, ester such as ethyl acetate, or the like.

Moreover, to recover omega 9 type highly polyunsaturated fatty acid directly, without first converting the fatty acid to its methyl ester, the above-mentioned extracted lipid is subjected to an alkalysis (for example, with 5% sodium hydroxide at room temperature for 2 to 3 hours), and the alkal-hydrolysate is extracted and the omega 9 type polyunsaturated fatty acid is purified, according to a conventional procedure.

Next, the present invention is further explained by Examples.

EXAMPLE 1

2 ml of a medium (pH 6.0) containing 2% or 4% glucose and 1% yeast extract was put into a 10 ml Erlenmeyer flask, and autoclaved at 120° C. for 20 minutes. *Mortierella alpina* mutant SAM 1861 was added, and cultured on a reciprocating shaker (110 rpm) at 12° C., 20° C. or 28° C. for 10 days.

After culturing the cultured cells were recovered by filtration, thoroughly washed with water and dried by a centrifuge evaporation at 60° C. for 2 hours. To the cells were added 2 ml methylene chloride and 2 ml anhydrous methanol/hydrochloric acid (10%), and the mixture was incubated at 50° C. for 3 hours to produce methyl esterified fatty acids. The reaction mixture was extracted twice with 4 ml n-hexane and 1 ml water and the cells remained in the reaction mixture. The solvent was distilled off in a centrifuge evaporation at 40° C. for 1 hour. The fatty acid methyl ester preparation thus prepared was analyzed by gas chromatography. The result is shown in Table 1.

TABLE 1

| Cult. Temp. (°C.) | Glucose Conc. (%) | Growth (g/l) | ω9PUFA produced (g/l) | | | Fatty acid composition[*] (%) | | | | | | |
|---|---|---|---|---|---|---|---|---|---|---|---|---|
| | | | 18:2 (ω9) | 20:2 (ω9) | 20:3 (ω9) | 16:0 PA | 18:0 SA | 18:1 OA | LA | 18:2 (ω9) | GLA | 20:1 |
| 12 | 2 | 11.1 | 0.30 | 0.07 | 0.57 | 4.0 | 5.0 | 43.7 | 0 | 12.3 | 0 | 4.1 |
| 12 | 4 | 16.1 | 0.39 | 0.08 | 0.69 | 3.9 | 5.7 | 43.6 | 0 | 12.5 | 0 | 4.0 |
| 20 | 2 | 10.0 | 0.39 | 0.07 | 0.56 | 4.8 | 5.8 | 36.8 | 0 | 16.2 | 0 | 3.0 |
| 20 | 4 | 15.0 | 1.14 | 0.18 | 1.30 | 5.5 | 6.1 | 35.7 | 0 | 19.1 | 0 | 2.7 |
| 28 | 2 | 10.0 | 0.27 | 0.04 | 0.22 | 1.0 | 5.1 | 53.7 | 0 | 15.2 | 0 | 3.2 |
| 28 | 4 | 15.4 | 0.83 | 0.16 | 0.77 | 9.3 | 7.3 | 42.6 | 0 | 13.5 | 0 | 2.5 |

| Cult. Temp. (°C.) | Glucose Conc. (%) | Growth (g/l) | ω9PUFA produced (g/l) | | | Fatty acid composition[*] (%) | | | | | | |
|---|---|---|---|---|---|---|---|---|---|---|---|---|
| | | | 18:2 (ω9) | 20:2 (ω9) | 20:3 (ω9) | 20:2 | 20:2 (ω9) | 20:3 (ω9) | DGLA | Ara | EPA | 24:0 |
| 12 | 2 | 11.1 | 0.30 | 0.07 | 0.57 | 0 | 3.0 | 23.3 | 0 | 0 | 0 | 1.9 |
| 12 | 4 | 16.1 | 0.39 | 0.08 | 0.69 | 0 | 2.6 | 22.0 | 0 | 0 | 0 | 2.8 |
| 20 | 2 | 10.0 | 0.39 | 0.07 | 0.56 | 0 | 2.8 | 23.7 | 0 | 0 | 0 | 3.8 |
| 20 | 4 | 15.0 | 1.14 | 0.18 | 1.30 | 0 | 3.3 | 21.7 | 0 | 0 | 0 | 2.9 |
| 28 | 2 | 10.0 | 0.27 | 0.04 | 0.22 | 0 | 2.0 | 12.3 | 0 | 0 | 0 | 4.4 |
| 28 | 4 | 15.4 | 0.83 | 0.16 | 0.77 | 0 | 2.6 | 12.4 | 0 | 0 | 0 | 6.1 |

[*]PA: palmitic acid, SA: stearic acid, OA: oleic acid, LA: Linoleic acid, 18:2(ω9): 6,9-octadecadienoic acid, GLA: γ-linolenic acid, 20:2(ω9): 8,11-eicosadienic acid, 20:3(ω9): Mead acid, DGLA: dihomo-γ-linolenic aid, Ara: Arachidonic acid, EPA: eicosapentaenoic acid, 20:1: 11-octadecanoic acid, 20:2: 11,14-eicosadienoic acid, 24:0: lignoceric acid

EXAMPLE 2

2.5 liters of a medium (pH 6.0) containing 2% glucose and 1% yeast extract was put into a 5 liter jar fermentor, and sterilized at 120° C. for 30 minutes. 40 ml of a pre-culture of *Mortierella alpina* mutant SAM 1861 was added, and the culturing was carried out at a temperature of 20° C., 24° C. or 28° C., at an aeration rate of 1 vvm for 7 days. Glucose was added daily at an amount of 1% per culture medium for 2 to 5 days of the culturing. After culturing, the cells were treated as described in Example 1 to esterify fatty acids produced, except that the procedures were carried out at a scale 500 times that of Example 1. The resulting fatty acid methyl ester preparation was analyzed by gas chromatography. The result is shown in Table 2.

TABLE 2

| Cult. Temp. (°C.) | Growth (g/l) | ω9PUFA produced (g/l) | | | Fatty acid composition (%) | | | | | | | | | | | | |
|---|---|---|---|---|---|---|---|---|---|---|---|---|---|---|---|---|---|
| | | 18:2 (ω9) | 20:2 (ω9) | 20:3 (ω9) | 16:0 PA | 18:0 SA | 18:1 OA | LA | 18:2 (ω9) | GLA | 20:1 | 20:2 | 20:2 (ω9) | 20:3 (ω9) | DGLA | Ara | EPA | 24:0 |
| 20 | 14.4 | 0.70 | 0.15 | 0.72 | 6.4 | 11.0 | 46.3 | 0 | 11.1 | 0 | 0.9 | 0 | 2.3 | 11.3 | 0 | 0 | 0 | 4.9 |
| 24 | 16.6 | 0.86 | 0.21 | 0.70 | 7.1 | 11.0 | 46.6 | 0 | 11.3 | 0 | 0.9 | 0 | 2.8 | 9.2 | 0 | 0 | 0 | 5.6 |

TABLE 2-continued

| Cult. Temp. (°C.) | Growth (g/l) | ω9PUFA produced (g/l) | | | Fatty acid composition (%) | | | | | | | | | | | | |
|---|---|---|---|---|---|---|---|---|---|---|---|---|---|---|---|---|---|
| | | 18:2 (ω9) | 20:2 (ω9) | 20:3 (ω9) | 16:0 PA | 18:0 SA | 18:1 OA | LA | 18:2 (ω9) | GLA | 20:1 | 20:2 | 20:2 (ω9) | 20:3 (ω9) | DGLA | Ara | EPA | 24:0 |
| 28 | 14.5 | 0.53 | 0.16 | 0.32 | 10.2 | 11.1 | 49.8 | 0 | 8.6 | 0 | 0.9 | 0 | 2.6 | 5.2 | 0 | 0 | 0 | 6.0 |

The fatty acid methyl ester mixture thus obtained was separated by high performance liquid chromatography using a reverse column ($5C_{18}$) and acetonitrile/water (85:15) as an eluting agent to isolate 6,9-octadecadienoic acid, 8,11-eicosadienoic acid, and 5,8,11-eicosatrienic acid (mead acid). The structures of these fatty acids were confirmed by Mass spectrum and NMR analysis.

EXAMPLE 3

A medium (pH 6.0) containing 2% glucose, 1% yeast extract, and 0.5% precursor for omega 9 type polyunsaturated fatty acid shown in Table 3 was used as described in Example 1. As a producer strain, *Mortierella alpina* mutant SAM 1861 was used. The results are shown in Table 3.

TABLE 3

| Additives | ω9PUFA* produced (g/l) | | |
|---|---|---|---|
| | 18:2 | 20:2 | 20:3 |
| None additive | 0.25 | 0.04 | 0.23 |
| Hexadecane | 0.35 | 0.06 | 0.34 |
| Octadecane | 0.41 | 0.06 | 0.41 |
| Palmitic acid | 0.43 | 0.07 | 0.44 |
| Stearic acid | 0.51 | 0.07 | 0.50 |
| Oleic acid | 0.62 | 0.11 | 0.60 |
| Sodium palmitate | 0.38 | 0.08 | 0.38 |
| Sodium stearate | 0.40 | 0.08 | 0.40 |
| Sodium oleate | 0.53 | 0.09 | 0.52 |
| Methyl Palmitate | 0.48 | 0.10 | 0.49 |
| Methyl stearate | 0.56 | 0.11 | 0.55 |
| Methyl oleate | 0.71 | 0.16 | 0.70 |
| Ethyl oleate | 0.72 | 0.15 | 0.71 |
| Palm oil | 0.49 | 0.08 | 0.48 |
| Olive oil | 0.52 | 0.12 | 0.50 |
| Coconut oil | 0.39 | 0.07 | 0.35 |

*18:2; 6,9-Octadecadienoic acid
20:2; 8,11-Eicosadienoic acid
20:3; 5,8,11-Eicosatrienoic acid (mead acid)

We claim:

1. A process for the production of omega 9 type polyunsaturated fatty acid having at least two double bonds and having 18 to 22 carbon atoms, comprising the steps of
   mutating a microorganism having the ability to produce arachidonic acid, wherein the microorganism belongs to the genus Mortierella and a species selected from the group consisting of *Mortierella elongata, Mortierella exiqua, Mortierella hygrophila,* or *Mortierella alpina;*
   selecting from the mutated microorganisms a mutated microorganism having Δ5 desaturase activity and Δ6 desaturase activity and having reduced or lost Δ12 desaturase activity, wherein the Δ12 desaturase activity is reduced in an amount sufficient to result in the production of omega 9 type polyunsaturated fatty acid;
   culturing the selected mutated microorganism under suitable conditions to provide for the production of omega 9 type polyunsaturated fatty acid; and
   recovering the omega 9 type polyunsaturated fatty acid.

2. A process for the production of omega 9 type polyunsaturated fatty acid according to claim 1, wherein the microorganism belongs to the species *Mortierella alpina.*

3. A process for the production of omega 9 type polyunsaturated fatty acid according to claim 1, wherein the selected mutated microorganism is *Mortierella alpina* SAM 1861.

4. A process for the production of a lipid containing omega 9 type polyunsaturated fatty acid having at least two double bonds and having 18 to 22 carbon atoms, comprising the steps of
   mutating a microorganism having the ability to produce arachidonic acid, wherein the microorganism belongs to the genus Mortierella and a species selected from the group consisting of *Mortierella elongata, Mortierella exiqua, Mortierella hygrophila,* or *Mortierella alpina;*
   selecting from the mutated microorganisms a mutated microorganism having Δ5 desaturase activity and Δ6 desaturase activity and having reduced or lost Δ12 desaturase activity, wherein the Δ12 desaturase activity is reduced in an amount sufficient to result in the production of omega 9 type polyunsaturated fatty acid;
   culturing the selected mutated microorganism under suitable conditions to provide for the production of a lipid containing omega 9 type polyunsaturated fatty acid; and
   recovering the lipid containing omega 9 type polyunsaturated fatty acid.

5. A process for the production of a lipid containing omega 9 type polyunsaturated fatty acid according to claim 4, wherein the microorganism belongs to the species *Mortierella alpina.*

6. A process for the production of a lipid containing omega 9 type polyunsaturated fatty acid according to claim 4, wherein the selected mutated microorganism is *Mortierella alpina* SAM 1861.

7. A process for the production of omega 9 type polyunsaturated fatty acid having at least two double bonds and having 18 to 22 carbon atoms, comprising the steps of
   mutating a microorganism having the ability to produce arachidonic acid, wherein the microorganism belongs to the genus Mortierella and a species selected from the group consisting of *Mortierella elongata, Mortierella exiqua, Mortierella hygrophila,* or *Mortierella alpina;*
   selecting from the mutated microorganisms a mutated microorganism having Δ5 desaturase activity and Δ6 desaturase activity and having reduced or lost Δ12 desaturase activity, wherein the Δ12 desaturase activity is reduced in an amount sufficient to result in the production of omega 9 type polyunsaturated fatty acid;
   culturing the selected mutated microorganism under suitable conditions to provide for the production of omega 9 type polyunsaturated fatty acid, in a medium supplemented with a precursor for omega 9 type polyunsaturated fatty acid selected from the group consisting of hydrocarbon, fatty acid, ester of fatty acid, salt of fatty acid and oil or fat containing such fatty acid at a concentration effective for microbial growth, or adding the precursor for omega 9 type polyunsaturated fatty acid at a concentration effective for microbial growth to a medium in which said microorganism has been cultured and further culturing the microorganism to produce omega 9 type polyunsaturated fatty acid; and recovering the lipid containing omega 9 type polyunsaturated fatty acid.

8. A process for the production of omega 9 type polyunsaturated fatty acid according to claim 7, wherein the microorganism belongs to the species *Mortierella alpina*.

9. A process for the production of omega 9 type polyunsaturated fatty acid according to claim 7, wherein the selected mutated microorganism is *Mortierella alpina* SAM 1861.

10. A process for the production of lipid containing omega 9 type polyunsaturated fatty acid having at least two double bonds and having 18 to 22 carbon atoms, comprising the steps of mutating a microorganism having the ability to produce arachidonic acid, wherein the microorganism belongs to the genus Mortierella and a species selected from the group consisting of *Mortierella elongata, Mortierella exiqua, Mortierella hygrophila,* or *Mortierella alpina;* selecting from the mutated microorganisms a mutated microorganism having $\Delta 5$ desaturase activity and $\Delta 6$ desaturase activity and having reduced or lost $\Delta 12$ desaturase activity, wherein the $\Delta 12$ desaturase activity is reduced in an amount sufficient to result in the production of omega 9 type polyunsaturated fatty acid;

culturing the selected mutated microorganism under suitable conditions to provide for the production of a lipid containing omega 9 type polyunsaturated fatty acid, in a medium supplemented with a precursor for omega 9 type polyunsaturated fatty acid selected from the group consisting of hydrocarbon, fatty acid, ester of fatty acid, salt of fatty acid and oil or fat containing such fatty acid at a concentration effective for microbial growth, or adding the precursor for omega 9 type polyunsaturated fatty acid at a concentration effective for microbial growth to a medium in which said microorganism has been cultured and further culturing the microorganism to produce a lipid containing omega 9 type polyunsaturated fatty acid; and recovering the lipid containing omega 9 type polyunsaturated fatty acid.

11. A process for the production of a lipid containing omega 9 type polyunsaturated fatty acid according to claim 10, wherein the microorganism belongs to the species *Mortierella alpina*.

12. A process for the production of a lipid containing omega 9 type polyunsaturated fatty acid according to claim 10, wherein the selected mutated microorganism is *Mortierella alpina* SAM 1861.

* * * * *